United States Patent [19]

Rauhut et al.

[11] 4,288,592

[45] Sep. 8, 1981

[54] PROCESS FOR PREPARING AMIDES BY REACTION IN PRESENCE OF MOLECULAR SIEVE

[75] Inventors: Michael M. Rauhut, Bridgewater; Shin-Shyong Tseng, Raritan, both of N.J.

[73] Assignee: American Cyanamid Company, Stamford, Conn.

[21] Appl. No.: 34,120

[22] Filed: Apr. 30, 1979

[51] Int. Cl.³ .............. C07C 103/34; C07C 103/737; C07C 103/76; C07C 143/74; C07C 143/77; C07C 143/78; C07C 143/83
[52] U.S. Cl. .................................. 544/159; 260/347.2; 260/347.3; 260/457; 260/459 A; 260/465 D; 544/168; 544/169; 546/246; 546/247; 546/282; 546/331; 546/336; 560/150; 562/426; 562/442; 562/553; 562/556; 564/61; 564/81; 564/96; 564/97; 564/123; 564/142; 564/143; 564/144
[58] Field of Search ........ 260/556 F, 556 AC, 465 D, 260/459 A, 513, 347.2, 347.3; 544/159; 560/150; 564/96, 97, 143

[56] References Cited

U.S. PATENT DOCUMENTS

| | | | |
|---|---|---|---|
| 3,558,698 | 1/1971 | Harrington et al. | 260/556 F |
| 3,609,187 | 9/1971 | Moore et al. | 260/556 F |
| 3,629,332 | 12/1971 | Harrington et al. | 260/556 F |
| 3,799,968 | 3/1974 | Harrington et al. | 260/556 F X |
| 3,865,844 | 2/1975 | Harrington et al. | 549/75 |
| 3,897,449 | 7/1975 | Harrington et al. | 548/306 |
| 3,920,444 | 11/1975 | Harrington et al. | 71/103 |

OTHER PUBLICATIONS

Breck, "Zeolite Molecular Sieves", p. 700 (1974).
Diehle, "Chem. Ab.", vol. 76, Ab. No. 84950q (1972).
Miyake et al., "Chem. Ab.", vol. 79, Ab. No. 18021y (1973).

*Primary Examiner*—John Doll
*Attorney, Agent, or Firm*—Gordon L. Hart

[57] ABSTRACT

There is provided a process for preparing amides which comprises reacting an amine, or an amide, and an acid halide, or anhydride, in suitable molecular proportions, in an inert organic diluent, in the presence of an effective amount of a molecular sieve, until the reaction is completed, separating the molecular sieve, and recovering the amide from the organic mother liquor.

9 Claims, No Drawings

PROCESS FOR PREPARING AMIDES BY REACTION IN PRESENCE OF MOLECULAR SIEVE

This invention was made under U.S. Government Contract N00014-77-0634 and is subject to provisions of ASPR 7-104.18 December 1969 and ASPR 7-302.23 (b) long form August 1977.

The present invention relates to a process for preparing amides, more particularly N,N'-bis(trifluoromethylsulfonyl)oxamide compounds, which are useful for generating chemiluminescence by reaction with a hydroperoxide.

The preparation of amides by the reaction of amines or amides with acid halides, or anhydrides, in the presence of an acid-binding agent, is well-known in the art. Methods for the preparation of trifluoromethanesulfonanilides and N-substituted trifluoromethanesulfonamides, in particular, are disclosed by Harrington et al., U.S. Pat. Nos. 3,558,698; 3,629,332; 3,799,968; 3,865,844; 3,897,449; 3,920,444; and Moore et al., U.S. Pat. No. 3,609,187. While the processes disclosed hitherto can be used to prepare the desired amides and sulfonamides, there is a need for an improved process that will facilitate the preparation, by eliminating the need for the removal of reaction by-products by subsequent washing with dilute acid and extraction with dilute aqueous caustic soda, before recovering the product.

SUMMARY OF THE INVENTION

In accordance with the present invention, there is provided a process for preparing amides which comprises reacting an amine, or an amide, and an acid halide, or anhydride, in suitable molecular proportions, in an inert organic diluent, in the presence of an effective amount of a molecular sieve, until the reaction is completed, separating the molecular sieve, and recovering the amide from the organic mother liquor.

Preferably, the molecular sieve is powdered potassium aluminosilicate of the formula (I)

wherein Y represents an indefinite number, having a pore mesh diameter of about 3–5 angstroms, and it is used in about 1–2 parts by weight per part by weight of amine, or amide.

Preferably, the amide is a compound represented by formula (II)

wherein R represents hydrogen; alkyl of 1 to 6 carbon atoms; cycloalkyl of 4 to 8 carbon atoms; substituted alkyl or cycloalkyl wherein the substituents are selected from halo, carboxy, alkoxy, or alkoxycarbonyl, wherein the alkoxy is of 1 to 6 carbon atoms; alkanoyl of 2 to 18 carbon atoms; aroyl of 7 to 11 carbon atoms; aralkyl of 7 to 11 carbon atoms; carbocyclic aryl of 6 to 10 carbon atoms; heterocyclic aryl of 3 to 9 carbon atoms; substituted carbocyclic and heterocyclic aryl of 6 to 10 and 3 to 9 carbon atoms, respectively, wherein the substituents, one or more, are selected from halo, nitro, cyano, trifluoromethyl, alkyl and alkoxy of 1 to 6 carbon atoms, hydroxy, phenoxy, benzyloxy, phenyl, alkanoylamino of 2 to 6 carbon atoms, benzoylamino, alkylsulfonyl of 1 to 6 carbon atoms, carboxy, alkoxycarbonyl and alkoxysulfonyl wherein the alkoxy group has 1 to 6 carbon atoms, $-SO_3^\ominus M^\oplus$ wherein $M^\oplus$ is a cation selected from sodium, potassium, lithium, ammonium, monoalkylammonium, dialkylammonium, trialkylammonium, or tetraalkylammonium wherein the alkyl radicals have 1 to 6 carbon atoms, and may be the same or different, aminocarbonyl, and aminosulfonyl which are unsubstituted or substituted at the nitrogen by 1 or 2 radicals selected from alkyl of 1 to 6 carbon atoms, phenyl, or substituted phenyl wherein the substituents are as defined and the acid halide is oxalyl chloride.

The process of the present invention offers the following advantages over the prior art:
1. Bases, such as triethylamine, which may cause undesirable side reactions, are not required.
2. The reactions are carried out in a heterogeneous phase, thus simplifying the subsequent workup.
3. Acids produced during the reaction are rapidly adsorbed by the powdered molecular sieves, thus eliminating undesirable side reactions and by-products.
4. The molecular sieves also adsorb water, thus maximizing the anhydrous conditions for the reaction.
5. The molecular sieves can be reactivated for subsequent use.

DESCRIPTION OF PREFERRED EMBODIMENTS

The process of the present invention is readily carried out by reacting a suitable amine, or amide, with an acid halide, or anhydride, in suitable molecular proportions in an inert diluent in the presence of a suitable molecular sieve. Generally, the acid halide, or anhydride, is added dropwise to a suspension of amine, or amide, and molecular sieve in dichloromethane at room temperature, preferably under a nitrogen atmosphere. After the addition is completed, the reaction mixture is heated to a temperature high enough to dissolve any product which may have precipitated. Generally, the reaction is carried out at a temperature from about 0°–100° C., preferably about 25°–60° C., for a period of about 2–48 hours, preferably about 4–10 hours. The molecular sieves are then removed by filtration, or centrifugation, and the product is recovered from the mother liquor. The amount of molecular sieve used is usually about 1–2, preferably about 1.2–1.7, parts by weight per part by weight of amine or amide used. Purification of the crude product is effected by recrystallization or distillation.

As used herein, the term "suitable amine, or amide" is defined as an amine, or amide, which is soluble in the organic diluent under the conditions of the reaction. Suitable amines and amides include the following:
methylamine,
n-hexylamine,
cyclohexylamine,
dodecylamine,
2-chloroethylamine,
2-bromoethylamine,
2-methoxyethylamine,
2-n-hexyloxyethylamine,
diethylamine,
N-methylcyclohexylamine,
aniline,
p-chloroaniline, p-nitroaniline,
2,4-dichloroaniline,
2,4,6-trichloroaniline,
4-methoxy-2-methylaniline,
N-ethylaniline,
benzylamine,
o-methoxybenzylamine,
2,6-dichlorobenzylamine,
2-(2-pyridyl)ethylamine,
2-furanylethylamine,
2-thienylethylamine,
2-morpholylethylamine,
2-piperidylethylamine,
2-chloro-3-aminopyridine,
acetamide,
benzenesulfonamide,
4-chlorobenzenesulfonamide,
trifluoromethanesulfonamide,
N-phenyltrifluoromethanesulfonamide,
N-(4-chlorophenyl)trifluoromethanesulfonamide,
N-(2,4-dichlorophenyl)trifluoromethanesulfonamide,
N-(2,4,5-trichlorophenyl)trifluoromethanesulfonamide,
N-(2,4,6-trichlorophenyl)trifluoromethanesulfonamide,
N-(4-nitrophenyl)trifluoromethanesulfonamide,
N-(2-methoxyethyl)trifluoromethanesulfonamide,
N-methyltrifluoromethanesulfonamide,
N-(2-bromoethyl)trifluoromethanesulfonamide,
N-(2-chloro-3-pyridyl)trifluoromethanesulfonamide,
N-(2-chloroethyl)trifluoromethanesulfonamide,
N-(2-morpholylethyl)trifluoromethanesulfonamide,
N-(2-piperidylethyl)trifluoromethanesulfonamide,
N-(2-chloro-3-pyridyl)trifluoromethanesulfonamide,
and the sodium, potassium, lithium, ammonium, methylammonium, n-hexylammonium, diethylammonium, tri-n-butylammonium, and tetraethylammonium salts of:
N-(4-carboxyphenyl)trifluoromethanesulfonamide,
N-(2-carboxyphenyl)trifluoromethanesulfonamide,
N-(4-sulfophenyl)trifluoromethanesulfonamide, and
N-(2-sulfophenyl)trifluoromethanesulfonamide.

The preferred compounds of formula (II) are as follows:
N-phenyltrifluoromethanesulfonamide,
N-(4-chlorophenyl)trifluoromethanesulfonamide,
N-(2,4-dichlorophenyl)trifluoromethanesulfonamide,
N-(2,4,5-trichlorophenyl)trifluoromethanesulfonamide,
N-(2,4,6-trichlorophenyl)trifluoromethanesulfonamide,
N-(4-nitrophenyl)trifluoromethanesulfonamide,
N-(2-methoxyethyl)trifluoromethanesulfonamide, and
N-(2-chloro-3-pyridyl)trifluoromethanesulfonamide.

The particularly preferred compound of formula (II) is N-(2,4,5-trichlorophenyl)trifluoromethanesulfonamide.

Suitable acid halides include the following:
acetyl bromide,
isobutyryl chloride,
hexanoyl chloride,
crotonyl chloride,
cyclohexanecarbonyl chloride,
decanoyl chloride,
stearoyl chloride,
bromoacetyl bromide,
6-bromohexanoyl chloride,
3-chloropropionyl chloride,
methoxyacetyl chloride,
trichloroacetyl chloride,
phenylacetyl chloride,
phenoxyacetyl chloride,
p-bromophenylacetyl chloride,
p-nitrophenylacetyl chloride,
ethyloxalyl chloride,
benzoyl bromide,
p-chlorobenzoyl chloride,
p-octylbenzoyl chloride,
3,5-dinitrobenzoyl chloride,
o-methoxybenzoyl chloride,
p-cyanobenzoyl chloride,
p-toluoyl chloride,
p-pentyloxybenzoyl chloride,
1-naphthoyl chloride,
2-naphthoyl chloride,
p-iodobenzoyl chloride,
4-biphenylcarbonyl chloride,
isonicotinoyl chloride,
nicotinoyl chloride,
2-furanylcarbonyl chloride,
5-thiazoylcarbonyl chloride,
benzenesulfonyl chloride,
p-chlorobenzenesulfonyl chloride,
m-trifluoromethylbenzenesulfonyl chloride,
trifluoromethanesulfonyl chloride,
1-butanesulfonyl chloride,
2,5-dichlorobenzenesulfonyl chloride,
methanesulfonyl fluoride,
methanesulfonyl chloride,
1-naphthalenesulfonyl chloride,
2-naphthalenesulfonyl chloride,
m-nitrobenzenesulfonyl chloride,
α-toluenesulfonyl fluoride,
2-thiophenesulfonyl chloride,
trichloromethanesulfonyl chloride,
oxalyl chloride,
azelaoyl chloride,
sebacyl chloride,
succinyl chloride,
phthaloyl chloride,
isophthaloyl chloride,
m-(chlorosulfonyl)benzoyl chloride, and
m-benzenedisulfonyl chloride.

The preferred acid halides are oxalyl chloride and trifluoromethanesulfonyl chloride.

Suitable acid anhydrides include the following:
acetic anhydride,
hexanoic anhydride,
trifluoromethanesulfonic anhydride,
benzoic anhydride,
phthalic anhydride,
trifluoroacetic anhydride, and
methanesulfonic anhydride.

The preferred acid anhydrides are acetic anhydride, trifluoroacetic anhydride, methanesulfonic anhydride, benzoic anhydride, and trifluoromethanesulfonic anhydride.

Suitable inert organic diluents include:
dichloromethane,
1,2-dichloroethane,
carbon tetrachloride,
chloroform,
chlorobenzene,
toluene,
hexane,
dioxane,
acetone,
acetonitrile,
tetrahydrofuran, and the like.

Suitable molecular sieves include the zeolites, a group of hydrated aluminum and calcium, potassium, or sodium silicates capable of reacting with any acid liberated in the process. Suitable molecular sieves include those presently known in the art as Types 3A, 4A, 5A, and 13X, respectively. The preferred molecular sieve is powdered Type 3A, represented by formula (I), having a pore diameter of about 3–5 angstroms. After use, the molecular sieve is reactivated by heating in a muffle furnace at about 400° C.

The following examples illustrate the process of this invention. All parts are by weight unless otherwise indicated.

EXAMPLE 1

Preparation of
N-(2,4,5-Trichlorophenyl)trifluoromethanesulfonamide

Trifluoromethanesulfonic anhydride (28.2 g; 0.1 mole) is added portionwise into a stirred suspension of 2,4,5-trichloroaniline (19.6 g; 0.1 mole) and powdered Type 3A molecular sieves (20 g; Union Carbide Corporation) in dichloromethane (150 mls) at 0° C. under a nitrogen atmosphere. After the addition is completed, the mixture is stirred at room temperature for 18 hours. The reaction mixture is then filtered and the solid is further washed with warm dichloromethane. Evaporation of the filtrate gives 22.31 grams (68% of theoretical) of crude product which, after recrystallization from methylcyclohexane, melts at 104°–106° C.

In the manner described above, using 0.1 mole of the appropriately substituted anilines, and amines, the following trifluoromethanesulfonamides are prepared:
N-phenyltrifluoromethanesulfonamide,
N-(4-chlorophenyl)trifluoromethanesulfonamide,
N-(2,4-dichlorophenyl)trifluoromethanesulfonamide,
N-(2,4,6-trichlorophenyl)trifluoromethanesulfonamide,
N-(4-nitrophenyl)trifluoromethanesulfonamide,
N-(2-methoxyethyl)trifluoromethanesulfonamide,
N-methyltrifluoromethanesulfonamide,
N-(2-bromoethyl)trifluoromethanesulfonamide,
N-(2-morpholinoethyl)trifluoromethanesulfonamide,
and N-(2-piperidinoethyl)trifluoromethanesulfonamide.

EXAMPLE 2

Preparation of
N-(2-Chloro-3-pyridyl)trifluoromethanesulfonamide

To a suspension of 2-chloro-3-aminopyridine (5.14 g; 0.04 mole) and powdered Type 3A molecular sieves (10 g) in dichloromethane (60 mls) is added, in portions, trifluoromethanesulfonic anhydride (3.4 mls; 0.02 mole) at 0° C. under a nitrogen atmosphere. After the addition is completed, the mixture is stirred at room temperature for 5 hours and then filtered. The filtrate is evaporated, and the residue is treated with water to obtain the crude product (5.0 g; 96% of theoretical). Recrystallization of the crude product from cyclohexane affords the pure compound: m.p. 120°–122° C.

Calculated for $C_6H_4N_2SO_2ClF_3$: C, 27.69%; H, 1.54%; N, 10.77%; S, 12.31%; Cl, 13.46%; F, 21.92%; Found: C, 27.85%; H, 1.41%; N, 11.00%; S, 11.95%; Cl, 13.66%; F, 21.50%

EXAMPLE 3

Preparation of
N,N'-Bis(2-chloro-3-pyridyl)-N,N'-Bis(trifluoromethylsulfonyl)Oxamide Oxalyl chloride (0.762 gram; 0.006 mole) is added dropwise to a suspension of N-(2-chloro-3-pyridyl)-trifluoromethanesulfonamide (2.61 grams; 0.01 mole) and powdered Type 3A molecular sieves (5.0 grams) in dichloromethane (75 mls) at 0° C. under a nitrogen atmosphere. The mixture is then heated to 60° C., held thereat for 3 hours, and then stirred at room temperature for 60 hours. The reaction mixture is filtered and the filtrate is evaporated to dryness. The resulting residue is extracted with diethyl ether, and the combined ethereal extracts are dried over anhydrous sodium sulfate. The dried ethereal extract is then separated and evaporated to obtain 2.33 grams (81% of theoretical) of crude product.

Recrystallization of the crude product from cyclohexane gives the desired product, m.p. 104°–106° C.

Calculated for $C_{14}H_6N_4O_6Cl_2F_6S_2$: C, 29.27%; H, 1.05%; N, 9.76%; Cl, 12.20%; F, 19.86%; S, 11.15%; Found: C, 29.10%; H, 1.14%; N, 9.51%; Cl, 11.95%; F, 19.40%; S, 10.89%

In the manner described above using 0.01 mole of the appropriately substituted trifluoromethanesulfonamide, the following oxamides are prepared:
N,N'-bis(trifluoromethylsulfonyl)oxamide,
N,N'-bis(di-n-butyl)-N,N'-bis(trifluoromethylsulfonyl)oxamide,
N,N'-dihexanoyl-N,N'-bis(trifluoromethylsulfonyl)oxamide,
N,N'-bis(2-bromoethyl)-N,N'-bis(trifluoromethylsulfonyl)oxamide,
N,N'-bis(2-chloroethyl)-N,N'-bis(trifluoromethylsulonfyl)oxamide,
N,N'-bis(2-n-hexyloxyethyl)-N,N'-bis(trifluoromethylsulfonyl)oxamide,
N,N'-bis(dibenzyl)-N,N'-bis(trifluoromethylsulfonyl)oxamide,
N,N'-bis(2,6-dichlorobenzyl)-N,N'-bis(trifluoromethylsulfonyl)oxamide,
N,N'-bis([2-(2-pyridyl)ethyl]-N,N'-bis(trifluoromethylsulfonyl)oxamide,
N,N'-bis(2-furanyl)-N,N'-bis(trifluoromethylsulfonyl)oxamide,
N,N'-bis(2-thienyl)-N,N'-bis(trifluoromethylsulfonyl)oxamide,
N,N'-bis(4-aminocarbonylphenyl)-N,N'-bis(trifluoromethylsulfonyl)oxamide,
N,N'-bis(2-morpholinoethyl)-N,N'-bis(trifluoromethylsulfonyl)oxamide, and
N,N'-bis(2-piperidinoethyl)-N,N'-bis(trifluoromethylsulfonyl)oxamide.

EXAMPLE 4

Preparation of
N,N'-Bis(2,4,5-trichlorophenyl)-N,N'-Bis-(trifluoromethylsulfonyl)Oxamide.

Oxalyl chloride (4.44 grams; 0.035 mole) is added in portions to a suspension of N-2,4,5-trichlorophenyl trifluoromethylsulfonamide (15.0 grams; 0.06 mole) and powdered Type 3A molecular sieves (15 grams) in dichloromethane (150 mls) at 0° C. under a nitrogen atmosphere. After the addition is completed, the reaction mixture is heated to 60° C. and stirred thereat for 5 hours. The molecular sieves are then separated by filtration and the filtrate is concentrated to remove the dichloromethane and obtain 17.45 grams (82% of theoretical) of crude product.

Recrystallization of the crude product from methylcyclohexane gives the desired product.

EXAMPLE 5

Preparation of 2,4,5-Trichloroacetanilide

Acetyl chloride (2.13 mls; 0.03 mole) is added dropwise to a suspension of 2,4,5-trichloroaniline (4.91 g; 0.025 mole) and powdered 3A molecular sieves (7.4 g) in dichloromethane (25 mls), at room temperature, under a nitrogen atmosphere. When addition is completed, the mixture is heated to 50° C. for 1.5 hours and then cooled to room temperature. The 3A sieves are separated by filtration and washed with dichloromethane. All dichloromethane solutions are combined and evaporated to obtain 4.1 grams (69% of theoretical) of the solid product; m.p. 188°–190° C. after recrystallized from toluene.

Calculated for $C_8H_6ONCl_3$: C, 40.29%; H, 2.54%; N, 5.87%; Cl, 44.59%. Found: C, 40.05%; H, 2.60%; N, 5.65%; Cl, 44.30%

EXAMPLE 6

Preparation of Acetanilide Using Acetyl Chloride

Acetanilide is prepared by the method of Example 5 using 5.0 mls (0.055 mole) of aniline, 7.5 grams of Type 3A molecular sieves, and 4.58 mls (0.064 mole) of acetyl chloride. The crude product is recrystallized from toluene to obtain 5.87 grams (81% of theoretical) of pure acetanilide, m.p. 112°–114° C. (literature m.p. 114° C.).

EXAMPLE 7

Preparation of Acetanilide Using Acetic Anhydride

Acetanilide is prepared by the method of Example 5 using 5.0 mls (0.05 mole) of aniline, 7.5 grams of 3A molecular sieves and 6.6 g (0.065 mole) of acetic anhydride in 100 mls of methylene chloride. The crude product (6.23 grams; 86% of theoretical) is recrystallized from toluene to obtain pure acetanilide, m.p. 112°–114° C.

EXAMPLE 8

Preparation of Benzanilide

Benzanilide is prepared by the method of Example 5 using 5.0 mls (0.05 mole) of aniline, 7.5 grams of 3A molecular sieves and 7.48 mls (0.064 mole) of benzoyl chloride in 100 mls of dichloromethane. The separated 3A sieves (16.37 g) are extracted with 200 mls of hot 3A alcohol, and the alcohol extract is evaporated to dryness to obtain 7.24 grams (68% of theoretical) of crude benzanilide; m.p. 161°–163° C. after recrystallization from 3A alcohol. Dichloromethane filtrates from above reaction are evaporated to dryness and extracted with ethyl ether to obtain an additional 1.39 grams of crude benzanilide.

EXAMPLE 9

Preparation of Benzenesulfonanilide

Benzanilide is prepared by the method of Example 5 using 5.0 grams (0.05 mole) of aniline, 7.5 grams of powdered Type 3A molecular sieves and 8.2 mls (0.064 mole) of benzenesulfonyl chloride in 100 mls of dichloromethane. The crude product is recrystallized from petroleum ether to obtain 9.88 grams (79% of theoretical) of the pure compound, m.p. 104°–106° C. (literature m.p. 110° C.).

EXAMPLE 10

Preparation of Acetanilide Using Reactivated 3A Molecular Sieves

Acetanilide is prepared by the method of Example 6 using 7.5 grams of powdered Type 3A molecular sieves that had been used in a previous run and reactivated by heating overnight at 400° C. in a muffle furnace. Subsequent evaporation of the dichloromethane mother liquor gives 6.78 grams (94% of theoretical) of crude acetanilide which, after recrystallization from toluene, melts at 112°–114° C. (literature m.p. 114° C.).

EXAMPLE 11

Preparation of N-(2-chloroethyl)trifluoromethanesulfonamide

To a suspension of 2-chloroethylamine hydrochloride (5.8 g; 0.05 mole) and 15 grams of powdered Type 3A molecular sieves in 1,2-dichloroethane (100 mls) is added, in portions, trifluoromethanesulfonyl chloride (5.30 mls; 0.025 mole) at room temperature under a nitrogen atmosphere. After the addition is completed, the mixture is heated at 80° C. for 18 hours. The mixture is then filtered and the filtrate is evaporated to obtain 2.0 grams (19% of theoretical) of an oil. Vacuum distillation of this oil gives the pure product, b.p. 53°–55° C. (0.5 mm Hg).

Calculated for $C_3H_5NSO_2ClF_3$: C, 17.06; H, 2.37; N, 6.64; S, 15.17; Cl, 16.60; F, 27.01; Found: C, 17.42; H, 2.51; N, 6.54; S, 15,36; Cl, 16.35; F, 26.80

We claim:

1. A process for preparing amides which comprises reacting an amine, or amide, and an acid halide, or anhydride, in suitable molecular proportions, in an inert organic solvent, in the presence of an effective amount of a molecular sieve, until the reaction is completed, separating the molecular sieve and without another acid-binding agent, and recovering the amide from the organic mother liquor.

2. The process of claim 1 wherein the amount of molecular sieve used is about 1–2 parts by weight per part by weight of amine, or amide.

3. The process of claim 2 wherein the amount of molecular sieve used is about 1.2–1.7 parts by weight per part by weight of amine, or amide.

4. The process of claim 1 wherein the molecular sieve is powdered potassium aluminosilicate of the formula (I), $$K_{12}[(AlO_2)_{12}(SiO_2)_{12}] \cdot YH_2O \qquad (I)$$

with a pore mesh diameter of about 3–5 angstroms, wherein Y is an indefinite integer.

5. The process of claim 1 wherein the amide is a compound represented by formula (II)

(II)

wherein R represents hydrogen; alkyl of 1 to 6 carbon atoms; cycloalkyl of 4 to 8 carbon atoms; substituted alkyl or cycloalkyl wherein the substituents are selected from halo, carboxy, alkoxy, or alkoxycarbonyl, wherein the alkoxy is of 1 to 6 carbon atoms; alkanoyl of 2 to 18 carbon atoms; aroyl of 7 to 11 carbon atoms; aralkyl of 7 to 11 carbon atoms; carbocyclic aryl of 6 to 10 carbon atoms; heterocyclic aryl of 3 to 9 carbon atoms; substituted carbocyclic and heterocyclic aryl of 6 to 10 and 3 to 9 carbon atoms, respectively, wherein the substituents, one or more, are selected from halo, nitro, cyano, trifluoromethyl, alkyl and alkoxy of 1 to 6 carbon atoms, hydroxy, phenoxy, benzyloxy, phenyl, alkanoylamino of 2 to 6 carbon atoms, benzoylamino, alkylsulfonyl of 1 to 6 carbon atoms, carboxy, alkoxycarbonyl and alkoxysulfonyl wherein the alkoxy group has 1 to 6 carbon atoms, $-SO_3^{\ominus}M^{\oplus}$ wherein $M^{\oplus}$ is a cation selected from sodium, potassium, lithium, ammonium, monoalkylammonium, dialkylammonium, trialkylammonium, or tetraalkylammonium wherein the alkyl radicals have 1 to 6 carbon atoms, and may be the same or different, aminocarbonyl, and aminosulfonyl which are unsubstituted or substituted at the nitrogen by 1 or 2 radicals selected from alkyl of 1 to 6 carbon atoms, phenyl, or substituted phenyl wherein the substituents are as defined above for carbocyclic and heterocyclic aryl, and the acid halide is oxalyl chloride.

6. The process of claim 5 wherein the amount of molecular sieve used is about 1-2 parts by weight per part by weight of compound of formula (II).

7. The process of claim 6 wherein the molecular sieve is powdered potassium aluminosilicate of formula (I) with a pore mesh diameter of about 3-5 angstroms.

8. The process according to claim 1 wherein the molecular sieve used has been reactivated by heating at an elevated temperature.

9. The process according to claim 5 wherein the molecular sieve used has been reactivated by heating at an elevated temperature.

* * * * *

UNITED STATES PATENT OFFICE
CERTIFICATE OF CORRECTION

Patent No. 4,288,592             Dated  September 8, 1981

Inventor(s)  MICHAEL McKAY RAUHUT AND SHIN-SHYONG TSENG

It is certified that error appears in the above-identified patent and that said Letters Patent are hereby corrected as shown below:

Column 8, line 37, insert after "sieve," -- and without another acid-binding agent -- .

Column 8, line 38, delete "and without another".

Column 8, line 39, delete "acid-binding agent".

Signed and Sealed this

Fifteenth Day of December 1981

[SEAL]

Attest:

GERALD J. MOSSINGHOFF

*Attesting Officer*          *Commissioner of Patents and Trademarks*